(12) United States Patent
Chaki et al.

(10) Patent No.: US 8,946,380 B2
(45) Date of Patent: Feb. 3, 2015

(54) LIPOSOME ALLOWING LIPOSOME-ENTRAPPED SUBSTANCE TO ESCAPE FROM ENDOSOME

(75) Inventors: Shinji Chaki, Gunma (JP); Shigetada Chaki, legal representative, Nagano (JP); Kentaro Kogure, Hokkaido (JP); Shiroh Futaki, Kyoto (JP); Hideyoshi Harashima, Hokkaido (JP)

(73) Assignee: Japan Science and Technology Agency, Kawaguchi (JP)

( * ) Notice: Subject to any disclaimer, the term of this patent is extended or adjusted under 35 U.S.C. 154(b) by 239 days.

(21) Appl. No.: 11/652,865

(22) Filed: Jan. 12, 2007

(65) Prior Publication Data

US 2007/0299244 A1    Dec. 27, 2007

Related U.S. Application Data

(63) Continuation of application No. PCT/JP2005/012860, filed on Jul. 12, 2005.

(30) Foreign Application Priority Data

Jul. 12, 2004   (JP) .................................. 2004-205217

(51) Int. Cl.
| | |
|---|---|
| A61K 38/28 | (2006.01) |
| C07K 1/00 | (2006.01) |
| A61K 9/127 | (2006.01) |
| C07K 5/00 | (2006.01) |
| C07K 19/00 | (2006.01) |
| C07K 17/00 | (2006.01) |
| C07K 14/00 | (2006.01) |
| C07K 7/00 | (2006.01) |
| C07K 16/00 | (2006.01) |

(52) U.S. Cl.
CPC . *A61K 9/127* (2013.01); *C07K 5/00* (2013.01); *C07K 19/00* (2013.01); *A61K 38/28* (2013.01); *C07K 17/00* (2013.01); *C07K 14/00* (2013.01); *C07K 7/00* (2013.01); *C07K 16/00* (2013.01); *C07K 1/00* (2013.01)
USPC ........ 530/303; 530/350; 530/394; 530/387.1; 536/22.1

(58) Field of Classification Search
CPC ............ A61K 38/28; C07K 1/00; C07K 5/00; C07K 7/00; C07K 14/00; C07K 16/00; C07K 17/00; C07K 19/00; C07K 21/00
USPC ............... 530/303, 394, 350, 387.1; 536/22.1
See application file for complete search history.

(56) References Cited

U.S. PATENT DOCUMENTS

| | | | | |
|---|---|---|---|---|
| 5,264,221 | A * | 11/1993 | Tagawa et al. ................ | 424/450 |
| 6,245,427 | B1 | 6/2001 | Duzgunes et al. | |
| 2001/0007666 | A1 * | 7/2001 | Hoffman et al. .............. | 424/400 |
| 2003/0224037 | A1 | 12/2003 | Eriguchi et al. | |
| 2006/0281677 | A1 * | 12/2006 | Albarran et al. ................ | 514/12 |
| 2007/0098702 | A1 * | 5/2007 | Megeed et al. ............ | 424/93.21 |

FOREIGN PATENT DOCUMENTS

| | | |
|---|---|---|
| EP | 0354855 A2 | 2/1990 |
| JP | H1-249717 | 10/1989 |
| JP | 149512 | 6/1990 |
| JP | H2-149512 | 6/1990 |
| JP | 346918 | 12/1999 |
| JP | H4-346918 | 12/1999 |
| JP | 2002-500201 | 1/2002 |
| JP | 500201 | 1/2002 |
| JP | 2004-10481 | 1/2004 |
| JP | 10481 | 1/2004 |
| WO | WO-9738010 A2 | 10/1997 |
| WO | WO-9738010 A2 | 10/1997 |
| WO | WO 9738010 A2 * | 10/1997 |
| WO | 99/20252 A1 | 4/1999 |
| WO | WO-9934831 A1 | 7/1999 |
| WO | WO 0249676 A2 * | 6/2002 |
| WO | WO 02088318 A2 * | 11/2002 |

OTHER PUBLICATIONS

Subbarao et al., Biochemistry. Jun. 2, 1987;26(11):2964-7.*
Kakudo et al., Biochemistry. May 18, 2004;43:5618-5628.*
Goormaghtigh et al., Eur J Biochem. 1991;421-429.*
Fattal et al., Biochemistry. May 31, 1994;33(21):6721-31, Abstract Only.*
Parente et al., Biochemistry. Sep. 18, 1990;29(37):8713-9.*
Futaki et al., (J Gene Med. 2005;7:1450-1458).*
Kakudo et al., (Biochemistry. 2004;43(19):5618-5628).*
Simoes et al., (Gene Therapy. 1998;(5):955-964).*
Yamada et al., (Intl J Pharmaceutics. 2005;303:1-7).*
Managit et al., (Intl J Pharmaceutics. 2003;266:77-84).*
S. Simoes et al., "Gene delivery by negatively charged ternary complexes of DNA, cationic liposomes and transferrin or fusigenic peptides", Gene Therapy, vol. 5, pp. 955-964 (1998).

(Continued)

*Primary Examiner* — Cherie M Stanfield
(74) *Attorney, Agent, or Firm* — Edwards Wildman Palmer LLP; Peter F. Corless

(57) ABSTRACT

With the aim of providing a liposome, having a hydrophilic polymer introduced into the outer surface of the liposome membrane, which is a liposome capable of allowing the liposome-entrapped substance to escape from the endosome and be released into the cytoplasm, a liposome membrane component bound to the peptide shown by (a) or (b) below and a liposome membrane component bound to one end of a hydrophilic polymer the other end of which is bound to the peptide shown by (a) or (b) below are included in the liposome:

(a) a peptide comprising the amino acid sequence of SEQ ID NO:1;

(b) a peptide comprising the amino acid sequence of SEQ ID NO:1 with 1 or more amino acids deleted, replaced or added therein, and capable of fusing lipid membranes with one another under acidic conditions.

13 Claims, No Drawings

(56) References Cited

OTHER PUBLICATIONS

K. Kono et al., "Design of fusogenic liposomes using a poly(ethylene glycol) derivative having amino groups", Journal of Controlled Release, vol. 68, pp. 225-235 (2000).

Kakudo, T. et al., Seitaimaku to Yakubutsu no Sogo Sayo Symposium Koen Yoshishu, 2001, 189-192.

Saki, N. et al., Drug Deliv. Syst., 2003, 18(3), p. 241 I-B-4.

Kakudo, T. et al., Seitaimaku to Yakubutsu no Sogo Sayo Symposium Koen Yoshishu, 2001, 189-192 (English translation provided).

Managit, C. et al., Nippon Yakugakukai Nenkai Koen Yoshishu, 2002, p. 64, 26[P] II-408.

Parente, R.A., et al., Mechanism of Leakage of Phospholipid Vesicle Contents Induced by the Peptide, Biochemistry, 1990, vol. 29, pp. 8720-8728.

Parente, R.A., et al., pH-dependent Fusion of Phosphatidylcholine Small Vesicles, the Journal of Biological Chemistry, 1988, vol. 263, pp. 4724-4730.

Kuehne, J. et al., Synthesis and Characterization of Membrane-Active Gala-OKT9 Conjugates, Bioconjugate Chem., 2001, vol. 12, pp. 742-749.

Li, W., et al, Gala: a designed synthetic pH-responsive amphipathic peptide with applications in drug and gene delivery, Advanced Drug Delivery Reviews 56 (2004), pp. 967-985.

Turk, Mj, et al., Characterization of a novel p-H sensitive peptide that enhances drug release from folate-targeted liposomes at endosomal pHs, Biochimica et Biophysica Acta 1559 (2002), pp. 56-68.

Kakudo, T. et al., Seitaimaku to Yakubutsu no. Sogo Sayo Symposium Koen Yoshishu, 2001, 189-192 (English translation provided).

Managit, C. et al., Nippon Yakugakukai Nenkai Koen Yoshishu, 2002, p. 64, 26[P] 11-408.

Saki, N. et al., Drug Deliv. Syst., 2003, 18(3), p. 241 I-B-4 (English translation provided).

\* cited by examiner

LIPOSOME ALLOWING LIPOSOME-ENTRAPPED SUBSTANCE TO ESCAPE FROM ENDOSOME

CROSS-REFERENCE TO RELATED APPLICATIONS

This application is a continuation of PCT/JP2005/012860, filed on Jul. 12, 2005, which in turn claims priority from Japanese application no. 2004-205217, filed Jul. 12, 2004, the contents of which are incorporated herein by reference.

TECHNICAL FIELD

The present invention relates to a liposome having a functional molecule introduced into the outer surface of the liposome membrane.

BACKGROUND ART

In recent years there has been much development of liposomes comprising functional molecules introduced into the surface of the liposome membrane as vectors for delivering drugs, nucleic acids, proteins, sugars or other substances to target sites.

For example, liposomes have been developed comprising hydrophilic polymers (for example, polyalkylene glycols such as polyethylene glycol) introduced into the outer surface of the liposome membrane (Japanese Patent Applications Laid-open Nos. H1-249717, H2-149512, H4-346918, 2004-10481). With these liposomes, it is possible to improve the directionality of the liposome for tumor cells by improving the retention of the liposome in blood.

Moreover, liposomes have been developed having introduced into the outer surface of the liposome membrane a substance (such as transferrin, insulin, folic acid, hyaluronic acid, an antibody or fragment thereof or a sugar chain) capable of binding to a receptor or antigen present on the surface of the cell membrane (Japanese Patent Applications Laid-open Nos. H4-346918, 2004-10481). With these liposomes it is possible to improve the endocytosis efficiency of the liposome.

Liposomes have also been developed using cholesterol bound to GALA in which GALA is introduced into the outer surface of the liposome membrane (T. Kakudo et al., Biochemistry, 2004, Vol. 43, pp. 5618 to 5623). A liposome becomes enveloped by endosome in the process of endocytosis, and inside the endosome the liposome is broken down when the endosome fuses with the lysosome, but with this kind of liposome the liposome-entrapped substance can escape from the endosome and be released into the cytoplasm.

GALA is a synthetic peptide comprising the amino acid sequence represented by SEQ ID NO:1, which was synthesized by the group of Szoka et al (N. K. Subbarao et al, Biochemistry, 1987, Vol. 26, pp. 2964 to 2972) and has been much studied since then.

GALA is pH sensitive, assuming a random coil structure at a pH of 7.4, but when the pH rises to about 5.0 the charge of the glutamic acid residue is neutralized, extinguishing the electrical repulsion and producing an α helix structure (N. K. Subbarao et al., Biochemistry, 1987, Vol. 26, pp. 2964 to 2972). The proportion of α helix structures is about 20% at pH 7.4 but rises to about 70% when the pH rises to 5.0 (E. Goormaghtigh et al., European Journal of Biochemistry, 1991, Vol. 195, pp. 421 to 429).

When GALA is incubated under acidic conditions with liposomes comprising egg-yolk phosphatidylcholine, the liposome-entrapped substance leaks out (an effect which is strongest at pH 5.0), and the liposomes fuse with one another (R. A. Parente et al., Journal of Biological Chemistry, 1988, Vol. 263, pp. 4724 to 4730). Regarding the mechanism by which GALA causes the release of the liposome-entrapped substance, the suggestion is that when GALA penetrates the liposome membrane, the GALA penetrating the liposome membrane clumps in groups of 8 to 12 in the membrane, forming pores 5 to 10 Å in diameter (R. A. Parente et al., Biochemistry, 1990, Vol. 29, pp. 8720 to 8728).

DISCLOSURE OF THE INVENTION

It is an object of the present invention to provide a liposome having a hydrophilic polymer introduced into the outer surface of the liposome membrane, which is a liposome capable of allowing the liposome-entrapped substance to escape from the endosome and be released into the cytoplasm.

The inventors in this case perfected the present invention when they discovered that when GALA and a hydrophilic polymer without terminal GALA are introduced into the outer surface of a liposome membrane using a liposome membrane component bound to GALA and a liposome membrane component bound to one end of a hydrophilic polymer the other end of which is not bound to GALA, the liposome-entrapped substance cannot escape from the endosome even if the liposome-entrapped substance has a low molecular weight (see Comparative Example 1), and that when a hydrophilic polymer having terminal GALA is introduced into the outer surface of a liposome membrane using a liposome membrane component bound to one end of a hydrophilic polymer the other end of which is bound to GALA without using a liposome membrane component bound to GALA, the liposome-entrapped substance cannot escape from the endosome even if the liposome-entrapped substance has a low molecular weight (see Comparative Example 2), but that when GALA and a hydrophilic polymer having terminal GALA are introduced into the outer surface of a liposome membrane using a liposome membrane component bound to GALA and a liposome membrane component bound to one end of a hydrophilic polymer the other end of which is bound to GALA, the liposome-entrapped substance can escape from the endosome and be released into the cytoplasm even if the liposome-entrapped substance has a high molecular weight (see Example 1).

That is, the liposome of the present invention is a liposome comprising a liposome membrane component bound to peptide shown by (a) or (b) below and a liposome membrane component bound to one end of a hydrophilic polymer the other end of which is bound to the peptide shown by (a) or (b) below:

(a) A peptide comprising the amino acid sequence of SEQ ID NO:1 (sometimes called "peptide (a)" below);

(b) A peptide comprising the amino acid sequence of SEQ ID NO:1 with 1 or more amino acids deleted, replaced or added therein, and capable of fusing lipid membranes with one another under acidic conditions (sometimes called "peptide (b)" below).

It is believed that when the liposome of the present invention is in an endosome, the liposome membrane and endosome membrane are brought close together by the effect on the endosome membrane of peptide (a) or (b) bound to the end of the hydrophilic polymer, so that the peptide (a) or (b) bound to the liposome membrane component acts on the endosome membrane, causing the liposome membrane and endosome membrane to fuse together, with the effect that the liposome-entrapped substance escapes from the endosome and is released into the cytoplasm.

The liposome of the present invention has improved retention in blood due to the hydrophilic polymer introduced into the outer surface of the liposome membrane. Moreover, the liposome of the present invention is capable of allowing the liposome-entrapped substance to escape from the endosome and be released into the cytoplasm regardless of whether the liposome-entrapped substance is of low or high molecular weight.

BEST MODE FOR CARRYING OUT THE INVENTION

The present invention is explained in more detail below.

As long as it is a closed vesicle with a lipid bilayer structure, the liposome of the present invention may be a multilamellar vesicle (MLV) or a unilamellar vesicle such as a SUV (small unilamellar vesicle), LUV (large unilamellar vesicle) or GUV (giant unilamellar vesicle).

The liposome of the present invention is not particularly limited as to size but is preferably 30 to 1000 nm or more preferably 50 to 300 nm in diameter.

As long as it comprises a liposome membrane component bound to peptide (a) or (b) and a liposome membrane component bound to one end of a hydrophilic polymer the other end of which is bound to peptide (a) or (b), the liposome of the present invention may also comprise an unmodified liposome membrane component (that is, a liposome membrane component not bound to peptide (a) or (b) or to a hydrophilic polymer or the like), a liposome membrane component bound to one end of a hydrophilic polymer the other end of which is bound to a substance capable of binding to a receptor or antigen present on the surface of the cell membrane (hereunder sometimes called a "cell membrane binding substance"), or a liposome membrane component bound to one end of a hydrophilic polymer the other end of which is free (that is a hydrophilic polymer the other end of which is not bound to peptide (a) or (b), a cell membrane binding component or the like), etc.

The liposome of the present invention preferably comprises a liposome membrane component bound to one end of a hydrophilic polymer the other end of which is bound to a cell membrane binding substance. In this way, it is possible to effectively improve the endocytosis efficiency of the liposome of the present invention.

The liposome of the present invention preferably comprises a liposome membrane component bound to one end of a hydrophilic polymer the other end of which is free. The retention in blood of the liposome of the present invention in vivo can be adjusted by adjusting the compounded proportions of the liposome membrane component bound to one end of a hydrophilic polymer the other end of which is bound to peptide (a) or (b), a cell membrane binding substance and the like, and the liposome membrane component bound to one end of a hydrophilic polymer the other end of which is free.

The compounded amount of the liposome membrane component bound to peptide (a) or (b) is not particularly limited but is normally 0.1 to 10% or preferably 0.5 to 5% or more preferably 0.5 to 2% (mole ratio) of the total compounded amount of liposome membrane components. If the compounded amount of the liposome membrane component bound to peptide (a) or (b) is within this range, the liposome membrane and endosome membrane can be effectively fused to one other when the liposome of the present invention is inside the endosome.

The compounded amount of the liposome membrane component bound to one end of a hydrophilic polymer the other end of which is bound to peptide (a) or (b) is not particular limited but is normally 0.1 to 10% or preferably 0.5 to 5% or more preferably 0.5 to 2% (mole ratio) of the total compounded amount of liposome membrane components. If the compounded amount of the liposome membrane component bound to one end of a hydrophilic polymer the other end of which is bound to peptide (a) or (b) is within this range, the liposome membrane and endosome membrane can be effectively brought close to one another when the liposome of the present invention is inside the endosome.

The compounded amount of the unmodified liposome membrane component is not particularly limited but is normally 50 to 99% or preferably 70 to 99% or more preferably 85 to 95% (mole ratio) of the total compounded amount of liposome membrane components. If the compounded amount of the unmodified liposome membrane component is within this range, the liposome-entrapped substance can be effectively retained within the liposome.

The compounded amount of the liposome membrane component bound to one end of a hydrophilic polymer the other end of which is bound to a cell membrane binding substance is not particularly limited but is normally 0.01 to 50% or preferably 0.05 to 20% or more preferably 0.1 to 2% (mole ratio) of the total compounded amount of liposome membrane components. If the compounded amount of the liposome membrane component bound to one end of a hydrophilic polymer the other end of which is bound to a cell membrane binding substance is within this range, the endocytosis efficiency of the liposome of the present invention can be effectively improved.

The compounded amount of the liposome membrane component bound to one end of a hydrophilic polymer the other end of which is free is not particularly limited, but the combined compounded amount of the liposome membrane component bound to one end of a hydrophilic polymer the other end of which is bound to the peptide (a) or (b) and a cell membrane binding substance or the like and the liposome membrane component bound to one end of a hydrophilic polymer the other end of which is free is normally 0.5 to 50% or preferably 1 to 20% or more preferably 2 to 10% (mole ratio) of the total compounded amount of liposome membrane components. If the combined compounded amount is within this range, the retention in blood of the liposome of the present invention can be effectively improved in vivo.

In the liposome of the present invention, there are no particular limits on the types of membrane components as long as they do not interfere with lipid bilayer formation, and examples of liposome membrane components include lipids, membrane stabilizers, anti-oxidants, charged substances, membrane proteins and the like. Lipids are essential liposome membrane components, and the compounded amount thereof is normally 50 to 100% or preferably 70 to 100% or more preferably 85 to 100% (mole ratio) of the total compounded amount of liposome membrane components.

Examples of lipids include phospholipids, glycolipids, sterols, saturated and unsaturated fatty acids and the like.

Examples of phospholipids include phosphatidylcholines (such as dioleoyl phosphatidylcholine, dilauroyl phosphatidylcholine, dimyristoyl phosphatidylcholine, dipalmitoyl phosphatidylcholine, distearoyl phosphatidylcholine, etc.), phosphatidylglycerols (such as dioleoyl phosphatidylglycerol, dilauroyl phosphatidylglycerol, dimyristoyl phosphatidylglycerol, dipalmitoyl phosphatidylglycerol, distearoyl phosphatidylglycerol, etc.), phosphatidylethanolamines (such as dioleoyl phosphatidylethanolamine, dilauroyl phosphatidylethanolamine, dimyristoyl phosphatidylethanolamine, dipalmitoyl phosphatidylethanolamine, distearoyl phosphatidylethanolamine, etc.), phosphatidylserine, phosphatidylinositol, phosphatidic acid, cardiolipin, sphingomyelin, yolk lecithin, soy lecithin, hydrogenates of these and the like.

Examples of glycolipids include glyceroglycolipids (such as sulfoxyribosylglyceride, diglycosylglyceride, digalactosylglyceride, galatosyldiglyceride, glycosyldiglyceride), sphingoglycolipids (such as galactosylcerebroside, lactosylcerebroside, ganglioside) and the like.

Examples of sterols include animal sterols (such as cholesterol, cholesterol succinic acid, lanosterol, dihydrolanosterol, desmosterol, dihydrocholesterol), plant sterols (phytosterols, such as stigmasterol, sitosterol, campesterol, brassicasterol), microbial sterols (such as thymosterol, ergosterol) and the like.

Examples of saturated and unsaturated fatty acids include palmitic acid, oleic acid, stearic acid, arachidonic acid, myristic acid and other saturated or unsaturated fatty acids with 12 to 20 carbon atoms.

Membrane stabilizers are any liposome membrane components that can be added to physically or chemically stabilize the liposome membrane or adjust the fluidity of the liposome membrane, and the compounded amount thereof is normally 0 to 50% or preferably 0 to 45% or more preferably 0 to 40% (mole ratio) of the total compounded amount of liposome membrane components.

Examples of membrane stabilizers include sterols, glycerin or fatty acid esters thereof and the like.

Examples of sterols include specific examples such as those given above, while examples of fatty acid esters of glycerin include triolein, trioctanoin and the like.

Anti-oxidants are any liposome membrane components that can be added to prevent oxidation of the liposome membrane, and the compounded amount thereof is normally 0 to 10% or preferably 0 to 8% or more preferably 0 to 5% (mole ratio) of the total compounded amount of liposome membrane components.

Examples of anti-oxidants include tocopherol, propyl gallate, ascorbyl palmitate, butylated hydroxytoluene and the like.

Charged substances are any liposome membrane components that can be added to contribute a positive or negative charge to the liposome membrane, and the compounded amount thereof is normally 0 to 95% or preferably 0 to 80% or more preferably 0 to 70% (mole ratio) of the total compounded amount of liposome membrane components.

Examples of charged substances that contribute a positive charge include stearylamine, oleylamine and other saturated or unsaturated aliphatic amines and dioleoyl trimethyl ammonium propane and other saturated and unsaturated synthetic cationic lipids and the like, while examples of charged substances that contribute a negative charge include dicetyl phosphate, cholesteryl hemisuccinate, phosphatidylserine, phosphatidylinositol, phosphatidic acid and the like.

Membrane proteins are any liposome membrane components that can be added to maintain the structure of the liposome membrane or contribute functionality to the liposome membrane, and the compounded amount thereof is normally 0 to 10% or preferably 0 to 8% or more preferably 0 to 5% (mole ratio) of the total compounded amount of liposome membrane components.

Examples of membrane components include superficial membrane proteins, integral membrane proteins and the like.

The liposome membrane component bound to peptide (a) or (b) may be any of the liposome membrane components given as examples above, but is preferably a lipid or membrane stabilizer and more preferably a phospholipid, sterol or fatty acid. If the liposome membrane component bound to peptide (a) or (b) is a lipid or membrane stabilizer and especially if it is a phospholipid, sterol or fatty acid, the liposome membrane and endosome membrane can be effectively fused together when the liposome of the present invention is inside the endosome.

There are no particular limits on the type of liposome membrane component bound to one end of a hydrophilic polymer (regardless of whether the other end is bound to peptide (a) or (b), a cell membrane binding substance or the like), but it is preferably a lipid or membrane stabilizer and more preferably a phospholipid, sterol or fatty acid. If the liposome membrane component bound to one end of a hydrophilic polymer us a lipid or membrane stabilizer and particularly if it is a phospholipid, sterol or fatty acid, the retention in blood of the liposome of the present invention can be improved in vivo.

Peptide (a) is the synthetic peptide called "GALA", while peptide (b) is a mutant form of peptide (a). Peptides (a) and (b) are pH sensitive, and have the ability to fuse lipid membranes to one another in an acidic environment. Peptides (a) and (b) cannot fuse lipid membranes to one another in neutral or alkaline environments.

As long as it has a lipid bilayer structure, a lipid membrane may be either a liposome membrane or other artificial membrane or a cell membrane, endosome membrane or other biological membrane. Peptide (a) or (b) can mediate the fusion of artificial membranes to each other, the fusion of biological membranes to each other or the fusion of artificial membranes to biological membranes, and the liposome of the present invention employs the fusion of a liposome membrane to an endosome membrane mediated by peptide (a) or (b). The pH at which peptide (a) or (b) can fuse lipid membranes to one another is normally 3 to 6 or preferably 4 to 5.8 or more preferably 4.5 to 5.5.

There is no particular limit on the number or locations of the amino acids deleted, substituted or added in the amino acid sequence represented by SEQ ID NO:1 as long as peptide (b) retains the ability to fuse lipid membranes to each other in acidic environments, and the number of amino acids is one to multiple or preferably one to a few, with the specific range being normally 1 to 4 or preferably 1 to 3 or more preferably 1 to 2 in the case of deletion, normally 1 to 6 or preferably 1 to 4 or more preferably 1 to 2 in the case of substitution, and normally 1 to 12 or preferably 1 to 6 or more preferably 1 to 4 in the case of addition.

The type of hydrophilic polymer is not particularly limited as long as it serves to improve the retention in blood of the liposome in vivo, and examples of hydrophilic polymers include polyalkylene glycols (such as polyethylene glycol, polypropylene glycol, polytetramethylene glycol, polyhexamethylene glycol, etc.), dextran, pullulan, ficoll, polyvinyl alcohol, styrene-anhydrous maleic acid alternate copolymer, divinyl ether-anhydrous maleic acid alternate copolymer, amylose, amylopectin, chitosan, mannan, cyclodextrin, pectin, carrageenan and the like, but a polyalkylene glycol is preferred and polyethylene glycol is especially preferred.

When the hydrophilic polymer is a polyalkylene glycol, its molecular weight is normally 300 to 10,000 or preferably 500 to 10,000 or more preferably 1,000 to 5,000. If the molecular weight of the polyalkylene glycol is within this range, the retention in blood of the liposome can be effectively improved in vivo.

The hydrophilic polymer may have an introduced alkyl group, alkoxy group, hydroxyl group, carbonyl group, alkoxycarbonyl group, cyano group or other substitutional group.

Examples of alkyl groups include methyl, ethyl, n-propyl, isopropyl, n-butyl, isobutyl, s-butyl, t-butyl, n-pentyl, isopentyl, t-pentyl, neopentyl and other straight- or branched-chain alkyl groups with 1 to 5 carbon atoms.

Examples of alkoxy groups include methoxy, ethoxy, n-propoxy, isopropoxy, n-butoxy, isobutoxy, s-butoxy, t-butoxy and other straight- or branched-chain alkoxy group with 1 to 5 carbon atoms.

There are no particular limits on the type of substance capable of binding to a receptor or antigen on the surface of the cell membrane (cell membrane binding substance), but examples of cell membrane binding substances include transferrin, insulin, folic acid, hyaluronic acid, antibodies or fragments thereof, sugar chains, growth factors, apolipoproteins and the like.

Examples of growth factors include epithelial growth factor (EGF), insulin-like growth factor (IGF), fibroblast growth factor (FGF) and the like. Examples of apolipoproteins include apo A-1, apo B-48, apo B-100, apo E and the like. Examples of antibody fragments include Fab fragments, F(ab)'$_2$ fragments, single-chain antibodies (scfv) and the like.

The liposome membrane component and peptide (a) or (b) can be bound together via a covalent bond by means of a reaction between a functional group of the liposome membrane component (which may be a functional group artificially introduced into the liposome membrane component) and a functional group of peptide (a) or (b) (which may be a functional group artificially introduced into peptide (a) or (b)). Examples of combinations of functional groups capable of forming covalent bonds include amino/carboxyl groups, amino/halogenated acyl groups, amino/N-hydroxysuccinimido ester groups, amino/benzotriazole carbonate groups, amino/aldehyde groups, thiol/maleimide groups, thiol/vinyl sulfone groups and the like.

When using a thiol group of peptide (a) or (b), a thiol group of peptide (a) or (b) having the N-terminal amino group derivatized into —NH—CO—(CH$_2$)$_n$—SH (wherein n is an integer from 1 to 7) may be used for example. The thiol group of a cysteine residue introduced by substitution or addition into a terminal of peptide (b) may also be used.

The liposome membrane component may be bound to the N-terminal side of peptide (a) or (b), or to the C-terminal side. The peptide (a) or (b) bound to the liposome membrane component may also be a salt of a peptide, such as for example a peptide wherein the carboxyl group of the C-terminal (which does not participate in binding with the liposome membrane component) has been derivatized into —CO—NH$_2$.

The liposome membrane component and hydrophilic polymer can be bound together via a covalent bond by reacting a functional group of the liposome membrane component (which may be an functional group artificially introduced into the liposome membrane component) with a functional group of the hydrophilic polymer (which may be a functional group artificially introduced into the hydrophilic polymer). Examples of combinations of functional groups capable of forming covalent bonds include amino/carboxyl groups, amino/halogenated acyl groups, amino/N-hydroxysuccinimido ester groups, amino/benzotriazole carbonate groups, amino/aldehyde groups, thiol/maleimide groups, thiol/vinyl sulfone groups and the like.

The liposome membrane component may be bound to a terminal of a side chain of the hydrophilic polymer, but is preferably bound to a terminal of the main chain.

The hydrophilic polymer and peptide (a) or (b) can be bound together via a covalent bond by reacting a functional group of the hydrophilic polymer (which may be a functional group artificially introduced into the hydrophilic polymer) with a functional group of peptide (a) or (b) (which may be a functional group artificially introduced into peptide (a) or (b)). Examples of combinations of functional groups capable of forming covalent bonds include amino/carboxyl groups, amino/halogenated acyl groups, amino/N-hydroxysuccinimido ester groups, amino/benzotriazole carbonate groups, amino/aldehyde groups, thiol/maleimide groups, thiol/vinyl sulfone groups and the like.

When using a thiol group of peptide (a) or (b), a thiol group of peptide (a) or (b) having the amino group of the N-terminal derivatized into —NH—CO—(CH$_2$)$_n$—SH (wherein n is an integer from 1 to 7) may be used for example. The thiol group of a cysteine residue introduced by substitution or addition into the terminal of peptide (b) may also be used.

The hydrophilic polymer may be bound to the N-terminal side of peptide (a) or (b), or to the C-terminal side. The peptide (a) or (b) bound to the hydrophilic polymer may also be a salt of a peptide, such as for example a peptide wherein the carboxyl group of the C-terminal (which does not participate in binding with the hydrophilic polymer) has been derivatized into —CO—NH$_2$. Peptide (a) or (b) may be bound to a terminal of a side chain of the hydrophilic polymer, but is preferably bound to a terminal of the main chain.

The hydrophilic polymer and cell membrane binding substance can be bound together via a covalent bond by reacting a functional group of the hydrophilic polymer (which may be a functional group artificially introduced into the hydrophilic polymer) with a functional group of the cell membrane binding substance (which may be a functional group artificially introduced into the cell membrane binding substance). Examples of combinations of functional groups capable of forming covalent bonds include amino/carboxyl groups, amino/halogenated acyl groups, amino/N-hydroxysuccinimido ester groups, amino/benzotriazole carbonate groups, amino/aldehyde groups, thiol/maleimide groups, thiol/vinyl sulfone groups and the like.

When using a thiol group of the cell membrane binding substance, a thiol group of the cell membrane binding substance having an amino group derivatized into —NH—CO—(CH$_2$)$_n$—SH (wherein n is an integer from 1 to 7) may be used for example.

The cell membrane binding substance may be bound to a terminal of a side chain of the hydrophilic polymer, but is preferably bound to a terminal of the main chain.

Another peptide (a) or (b) may also be bound to whichever of the terminals (N terminal and C terminal) of peptide (a) or (b) is not involved in binding with the liposome membrane component or hydrophilic polymer. That is, a liposome membrane component bound to a fused protein comprising multiple peptides (a) or (b) may be used as the liposome membrane component bound to peptide (a) or (b), while a liposome membrane component bound to one end of a hydrophilic polymer the other end of which is bound to a fused peptide comprising multiple peptides (a) or (b) may be used as the liposome membrane component bound to one end of a hydrophilic polymer the other end of which is bound to peptide (a) or (b).

The liposome of the present invention can be prepared by a known method such as hydration, ultrasound treatment, ethanol injection, ether injection, reverse-phase evaporation, the surfactant method, freezing and thawing or the like. Liposomes with a fixed particle size distribution can be obtained by passing the liposomes through a pore size filter. Multimembrane liposomes may also be converted to single-membrane liposomes or single-membrane liposomes to multimembrane liposomes by ordinary methods.

The liposome of the present invention can entrap a target substance to be delivered to the interior of a cell.

There are no particular limits on the type of target substance, but examples include drugs, nucleic acids, peptides, proteins, sugars and complexes of these and the like, and these can be selected appropriately according to the object such as diagnosis, treatment or the like. The term "nucleic acids" encompasses DNA and RNA as well as analogs and derivatives of these (such as peptide nucleic acids (PNA), phosphorothioate DNA and the like). A nucleic acid may be single-stranded or double-stranded, and may be linear or circular.

When the target substance is water soluble, the target substance may be enclosed in a water phase within the liposome by adding the target substance to the aqueous solvent used to hydrate the lipid membrane in liposome manufacture. When the target substance is lipid soluble, the target substance may be enclosed within the lipid bilayer of the liposome by adding the target substance to the organic solvent used for manufacturing the liposome.

A liposome entrapping a target substance can be used as a vector for delivery of the target substance into a cell.

The cells into which the target substance is delivered are not particularly limited as to species, and may be from an animal, plant, microorganism or the like, but preferably they are animal cells and more preferably mammal cells. Examples of mammals include humans, monkeys, cows, sheep, goats, horses, pigs, rabbits, dogs, cats, rats, mice, guinea pigs and the like. The cells into which the target substance is delivered are also not particularly limited as to type, and may be somatic cells, reproductive cells, stem cells or cultured cells of these or the like.

The liposome of the present invention can be used for example as a dispersion. Physiological saline, phosphoric acid buffer, citric buffer, acetic acid buffer or another buffer can be used as the dispersion solvent. A sugar, polyvalent alcohol, water-soluble molecule, non-ionic surfactant, antioxidant, pH adjuster, hydration promoter or other additive may also be added to the dispersion.

The liposome of the present invention can be used as a dried (for example, freeze-dried, spray-dried, etc.) dispersion. The dried liposome may be made into a dispersion by addition of a buffer such as physiological saline, phosphoric acid buffer, citric buffer, acetic acid buffer or the like.

The liposome of the present invention may be used either in vivo or in vitro. When the liposome of the present invention is used in vivo, administration may be intravenous, intraperitoneal, subcutaneous, nasal or other parenteral administration, and the dosage and number of administrations can be adjusted appropriately according to the type and amount of target substance included in the liposome and the like.

EXAMPLES

The present invention is explained in detail below based on examples and comparative examples.

In the examples and comparative examples the various substances used in modifying the outer surface of the liposome membrane were prepared or obtained as follows.
(1) Preparation of GALA derivative (I) represented by Formula: Chol-O—CO—NH-GAL—CONH$_2$ (wherein Chol represents a cholesterol residue, —O— derives from a hydroxyl group of cholesterol, GAL is a GALA residue, —NH— derives from a GALA N-terminal amino group, and —CONH$_2$ derives from a GALA C-terminal carboxyl group)

GALA (SEQ ID NO:1) was synthesized by the Fmoc solid-phase method to obtain the GALA derivative (II) (molecular weight 3695.9) represented by Formula: NH$_2$-GAL-CO—NH-carrier (wherein GAL represents a GALA residue, —NH$_2$ represents a GALA N-terminal amino group, —CO— derives from a GALA C-terminal carboxyl group, —NH— derives from an amino group of the carrier, and the carrier is Rink amido resin (NovaBiochem).

GALA derivative (II) was washed with N,N-dimethylformamide (DMF) in a reaction vessel, and decompacted by being immersed in DMF and left for 20 minutes at room temperature. Cholesteryl chloroformate (Chol-O—COCl, molecular weight 449.1) in the amount of 3 equivalents of GALA derivative (II) was measured out and dissolved in 500 to 700 mL of DMF. Leaving a small amount of GALA derivative (II), the remaining GALA derivative (II) was added to the DMF solution of cholesteryl chloroformate, and triethylamine (TEA) was added in the amount of 3 equivalents of GALA derivative (II). This was done by first adding ⅓ the amount (1 equivalent) of TEA and agitating by rotation for 15 minutes at room temperature, then adding ⅓ the amount (1 equivalent) of TEA and agitating by rotation for 15 minutes at room temperature, and then finally adding the remainder (1 equivalent) of the TEA and agitating by rotation for 3 hours at room temperature. The reaction product was washed 5 times with DMF, 3 times with methanol and 3 times with diethyl ether. This reaction product was reacted with ninhydrin together with the GALA derivative (II) previously set aside, and the absence of a color change was confirmed. The GALA derivative (III) represented by Formula: Chol-O—CO—NH-GAL—CO—NH-carrier was obtained in this way.

Next, the reaction product was transferred to a fritted centrifuge tube, 0.2 mL of ethanedithiol (EDT) was added, and 0.8 mL of trifluoracetic acid (TFA) was then added (TFA: EDT =95:5) followed by 3 hours of agitation at room temperature. After agitation was complete, this was collected by suction filtration with a glass filter, and the TFA was removed with an evaporator. A gel state was confirmed, and diethyl ether was added in ice water and agitated for 20 minutes. The presence of a white, powdery solid was confirmed. This was then centrifuged for 5 minutes at 3,200 rpm, room temperature, and the supernatant was discarded and the remainder washed twice with diethyl ether. The supernatant was discarded again, and the remainder was suspended and dissolved in a 50% acetic acid solution, transferred to a 15 mL tube, covered with Milli Wrap and freeze dried. GALA derivative (I) was obtained in this way.

The resulting GALA derivative (I) was dissolved in DMF and centrifuged for 3 minutes at 12,000 rpm to precipitate the insoluble matter, and the supernatant was taken as the sample for high-performance liquid chromatography (HPLC) and subjected to reverse-phase HPLC under the following conditions to purify GALA derivative (I).

Column: cosmosil 5C$_4$-AR-300
Concentration gradient:
50B %→95B % (20 min), 95B %→95B % (20 min)
95B %→95B % (5 min, washing)
95B %→50B % (5 min, equilibration)
Flow rate: 2.0 mL/min
Temperature: Room temperature
Detection wavelength: 215 nm
HPLC was performed under the same conditions to confirm the purity of the fractioned sample, and the molecular weight of the sample was measured by MALDI-TOF MS. α-cyano-4-hydroxycinnamic acid (CHCA) was used as the matrix during molecular weight measurement.

(2) Preparation of GALA derivative (IV) represented by Formula: MPA-NH-GAL—CONH₂ (wherein MPA represents a 3-mercaptopropionyl group, GAL is a GALA residue, —NH— derives from a GALA N-terminal amino group, and —CONH₂ derives from a GALA C-terminal carboxyl group) The GALA derivative (I) purified by HPLC and N-hydroxysuccinimide 3-(2-pyridyldithio)priopionate (SPDP) were mixed in proportions of 1:2 (mole ratio) in a mixed solvent of DMF and water and reacted for 3 hours at 37° C., and reaction bi-products were removed using Sephadex G-25 Fine gel (Amersham Biosciences) to obtain a solution of the GALA derivative (V) represented by Formula: PDP—NH-GAL—CONH₂ (wherein PDP represents a 3-(2-pyridyldithio)priopionyl group, GAL is a GALA residue, —NH— derives from a GALA N-terminal amino group, and —CONH₂ derives from a GALA C-terminal carboxyl group). Next, dithiothreitol (DTT) was added to a final concentration of 50 mM, and this was reacted then for 30 minutes at room temperature and ultrafiltered with a microcon YM-3 (Millipore) to obtain a solution of GALA derivative (IV).

(3) Preparation of transferrin derivative (I)represented by MPA-NH-Tf (wherein MPA represents a 3-mercaptopropionyl group, Tf is a transferrin residue, and —NH— derives from an amino group of transferrin)

Transferrin and SPDP were mixed in proportions of 1:1.5 (mole ratio) in phosphate-buffered saline solution (PBS(-)), and reacted for 30 minutes at room temperature to obtain a solution of the transferrin derivative (II) represented by Formula: PDP-NH-Tf (wherein PDP represents a 3-(2-pyridylthio)propionyl group, Tf is a transferrin residue, and —NH— derives from an amino group of transferrin). DTT was added to a final concentration of 50 mM and reacted for 30 minutes at room temperature, and reaction by-products were removed with Sephadex G-25 Fine gel (Amersham Pharmacia) to obtain a solution of transferrin derivative (I).

(4) The polyethylene glycol derivative (I) (1,2-distearoyl-sn-glycero-3-phosphoethanolamin-N-[methoxy(polyethylene glycol)-2000]) represented by Formula: mPEG-CO—NH-DSPE (wherein mPEG represents a methoxy (polyethylene glycol) residue, DSPE represents a 1,2-distearoyl-sn-glycero-3-phosphoethanolamine residue, and —NH— derives from the amino group of 1,2-distearoyl-sn-glycero-3-phosphoethanolamine) was purchased from Avanti. The structural formula of polyethylene glycol derivative (I) is as follows:

[polyethylene glycol derivative (I)]

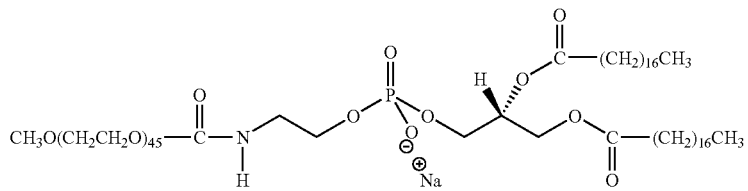

(5) The polyethylene glycol derivative (II) represented by Formula: Mal-PEG-CO—NH-DSPE (wherein Mal represents a maleimide group, PEG is a polyethylene glycol residue, DSPE is a 1,2-distearoyl-sn-glycero-3-phosphoethanolamine residue, and —NH— derives from the amino group of 1,2-distearoyl-sn-glycero-3-phosphoethanolamine) was purchased from NOF Corporation. The structural formula of polyethylene derivative (II) is as follows:

[polyethylene derivative (II)]

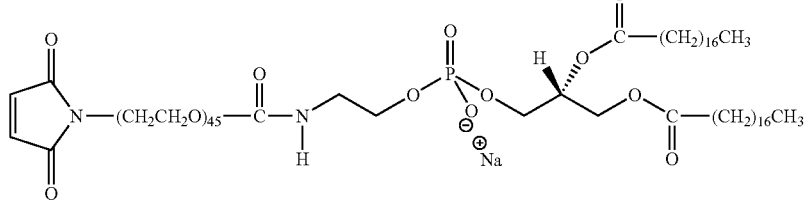

Example 1

(1) Liposome Preparation

Liposomes with a lipid composition of egg-yolk phosphatidylcholine (EPC):cholesterol:polyethylene glycol derivative (I):polyethylene glycol derivative (II)=2:1:0.12: 0.06 (mole ratio) were prepared by the REV method, and passed through membranes with pore sizes of 400 nm and 100 nm. Methoxy(polyethylene glycol) and polyethylene glycol having a terminal maleimide group are introduced into the outer surface of the liposome membrane at this stage.

The liposomes were prepared by the REV method as follows. The aforementioned lipid composition was dissolved in CHCl₃ to a final volume of 1 mL, 1 mL of diisopropyl ether was added and mixed with a vortex, and the mixture was separated into two quantities of 1 mL. 500 μL of sulforhodamine B (Rh) solution or a PBS(-) solution of fluorescein isothiocyanate-bovine serum albumin (FITC-BSA) was added to each, mixed with a vortex, and ultrasound treated for about 60 seconds for form an emulsion. After emulsion formation, a liposome solution was obtained by nitrogen gas evaporation.

Next, GALA derivative (I) was added to the liposome solution in the amount of 0.5 to 1% (mole ratio) of the total lipids forming the liposome membrane, and incubated for 1 hour at 37° C. GALA is introduced into the outer surface of the liposome membrane at this stage.

Next, GALA derivative (IV) and transferrin derivative (I) were added to the liposome solution, which was then O/N agitated at 4° C. At this stage, GALA derivative (IV) and transferrin derivative (I) are bound via —S— to a terminal maleimide group of the polyethylene glycol introduced into the outer surface of the liposome membrane.

In this way, a liposome was prepared having GALA, polyethylene glycol having terminal GALA, polyethylene glycol having terminal transferrin and polyethylene glycol having no terminal GALA or transferrin all introduced into the outer surface of the liposome membrane.

GALA derivative (I) and GALA derivative (IV) were used in the amounts of 0.5% or 1% (mole ratio) of the total lipids making up the liposome membrane. Transferrin derivative (I) was used in the amount of 0.5% (mole ratio) of the total lipids making up the liposome membrane.

A 5 mM Rh solution or 300 μM FITC-BSA solution (as FITC) was enclosed in liposomes in which the amount of GALA derivative (I) or (IV) was 0.5% mole, while a 400 μM FITC-BSA solution (as FITC) was enclosed in liposome in which the amount of GALA derivative (I) and GALA derivative (IV) was 1% mole.

(2) Liposome Introduction into Cells

Each kind of liposome was incubated for 18 hours at 37° C. in the presence of 5% $CO_2$ together with $1 \times 10^5$/mL K562 cells, which were then observed by confocal laser scanning microscopy (CLSM) to evaluate the number of cells with introduced liposomes, the number of cells with introduced liposomes in which the liposomes had achieved endocytosis, and the number of cells with introduced liposomes in which the liposome-entrapped substance (Rh or FITC-BSA) had escaped from the endosome and been released into the cytoplasm.

The results are shown in Table 1.

TABLE 1

|  | Added concentrations of GALA derivatives (I) and (IV) | |
| --- | --- | --- |
|  | 0.5% mole | 1% mole |
| Number of cells with introduced liposomes | 121 | 120 |
| Number of cells in which liposomes achieved endocytosis | 120 (99%) | 119 (99%) |
| Number of cells in which Rh was released into cytoplasm | 8 (7%) | — |
| Number of cells in which FITC-BSA was released into cytoplasm | 1 (1%) | 76 (63%) |

As shown in Table 1, the liposome-entrapped substance escaped from the endosome and was released into the cytoplasm regardless of whether the liposome-entrapped substance consisted of low-molecular-weight Rh or the like or high-molecular-weight BSA or the like.

Comparative Example 1

Liposomes were prepared as in Example 1 except that GALA derivative (IV) was not used. That is, the outer surface of the liposome membrane was modified as in Example 1 except that polyethylene glycol having terminal GALA was not introduced into the outer surface of the liposome membrane.

GALA derivative (I) was used in the amount of 1% mole of the total lipids making up the liposome membrane. A 5 mM Rh solution was enclosed in the liposomes.

The liposomes were incubated for 18 hours at 37° C. in the presence of 5% $CO_2$ together with $1 \times 10^5$/mL K562 cells, and observed by CLSM to evaluate the number of cells with introduced liposomes, the number of cells with introduced liposomes in which the liposomes had achieved endocytosis, and the number of cells with introduced liposomes in which the liposome-entrapped substance (Rh) had escaped from the endosome and been released into the cytoplasm.

The results are shown in Table 2.

TABLE 2

| Number of cells with introduced liposomes | 62 |
| --- | --- |
| Number of cells in which liposomes achieved endocytosis | 60 (97%) |
| Number of cells in which Rh was released in cytoplasm | 0 (0%) |

As shown in Table 2, the liposome-entrapped substance was unable to escape from the endosome even when they consisted of low-molecular-weight Rh or the like.

Comparative Example 2

Liposomes were prepared as in Example 1 except that GALA derivative (I) was not used. That is, the outer surface of the liposome membrane was modified as in Example 1 except that GALA was not introduced into the outer surface of the liposome membrane.

GALA derivative (IV) was used in the amount of 1% mole of the total lipids making up the liposome membrane. A 5 mM Rh solution was enclosed in the liposomes.

The liposomes were incubated for 18 hours at 37° C. in the presence of 5% $CO_2$ together with $1 \times 10^5$/mL K562 cells, and observed by CLSM to evaluate the number of cells with introduced liposomes, the number of cells with introduced liposomes in which the liposomes had achieved endocytosis, and the number of cells with introduced liposomes in which the liposome-entrapped substance (Rh) had escaped from the endosome and been released into the cytoplasm.

The results are shown in Table 3.

TABLE 3

| Number of cells with introduced liposomes | 100 |
| --- | --- |
| Number of cells in which liposomes achieved endocytosis | 95 (95%) |
| Number of cells in which Rh was released in cytoplasm | 0 (0%) |

As shown in Table 3, the liposome-entrapped substance was unable to escape from the endosome even when they consisted of low-molecular-weight Rh or the like.

The invention claimed is:

1. A liposome comprising:
   (a) a first liposome membrane component, bound to a first peptide comprising the amino acid sequence of SEQ ID NO:1;
   (b) a second liposome membrane component bound to one end of polyethylene glycol the other end of which is bound to a second peptide comprising the amino acid sequence of SEQ ID NO:1, and
   (c) a third liposome membrane component bound to one end of polyethylene glycol the other end of which is bound to the substance capable of binding to a receptor or antigen on the surface of a cell membrane, which liposome is capable of fusing to a cell membrane under acidic conditions, wherein the second peptide is bound via —S— to the other end of polyethylene glycol, and wherein the liposome is capable of releasing into the cytoplasm an entrapped target substance having a molecular weight ranging from low to high.

2. The liposome according to claim 1, wherein the substance capable of binding to a receptor or antigen on the surface of a cell membrane is transferrin, insulin, folic acid, hyaluronic acid, an antibody or fragment thereof, a sugar chain, a growth factor, or an apolipoprotein.

3. The liposome according to claim 1, further comprising
   (d) a fourth liposome membrane component bound to one end of polyethylene glycol the other end of which is free.

4. The liposome according to claim 1, encapsulating a target substance to be delivered to the inside of a cell.

5. The liposome according to claim 4, wherein the target substance is a drug, nucleic acid, peptide, protein, sugar, or combinations thereof.

6. The liposome according to claim 1, wherein the liposome is a vector for cellular delivery of a target substance.

7. The liposome according to claim 1, wherein the liposome is a multilamellar vesicle (MLV) or a unilamellar vesicle.

8. The liposome according to claim 7, wherein the unilamellar vesicle is a small unilamellar vesicle (SUV), a large unilamellar vesicle (LUV), or a giant unilamellar vesicle (GUV).

9. The liposome according to claim 1, wherein the liposome is 30 to 100 nm in the diameter.

10. The liposome according to claim 1, wherein the liposome is 50 to 300 nm in diameter.

11. The liposome according to claim 1, wherein the liposome membrane component is selected from the group consisting of a lipid, a membrane stabilizer, an antioxidant, a charged substance, and a membrane protein.

12. The liposome according to claim 11, wherein the lipid is selected from the group consisting of a phospholipid, a glycolipid, a sterol, a saturated fatty acid, and an unsaturated fatty acid.

13. The liposome according to claim 1, wherein the substance capable of binding to a receptor or antigen on the surface of cell membrane is transferrin.

* * * * *

SEQUENCE LISTING

```
<160> NUMBER OF SEQ ID NOS: 1

<210> SEQ ID NO 1
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30
```